United States Patent [19]

Button et al.

[11] 4,154,086

[45] May 15, 1979

[54] APPARATUS AND METHOD FOR THE DISCOVERY OF VOLATILE ORGANIC COMPOUNDS IN WATER

[75] Inventors: George E. Button, Pearland; Jeff R. Burke, Houston; Charles E. Dowden, Pasadena, all of Tex.

[73] Assignee: Petro-Tex Chemical Corporation, Houston, Tex.

[21] Appl. No.: 894,183

[22] Filed: Apr. 6, 1978

[51] Int. Cl.² .................................. G01N 33/00
[52] U.S. Cl. ................................................ 73/19
[58] Field of Search .................. 73/19, 23, 61.1 R; 23/230 HC, 232 R, 254 R

[56] References Cited

U.S. PATENT DOCUMENTS

| 3,037,374 | 6/1962 | Messinger | 73/61.1 R |
| 3,418,841 | 12/1968 | Issenmann | 73/19 |
| 3,681,028 | 8/1972 | Mason | 73/19 |
| 3,759,086 | 9/1973 | McAuliffe | 73/19 |
| 3,927,978 | 12/1975 | Wasik | 23/230 HC |

Primary Examiner—Stephen A. Kreitman
Attorney, Agent, or Firm—Kenneth H. Johnson

[57] ABSTRACT

An apparatus for discovery of trace amounts of volatile organic compounds, such as $C_3$ to $C_7$ hydrocarbons in water comprising a column having a lower zone containing a heating means, a sample water outlet means and a carrier gas inlet means located therein, an intermediate zone containing a sample water inlet means and condenser located therein, said sample water inlet means being located below said condenser and an upper zone having a gas detection means connected thereto.

10 Claims, 1 Drawing Figure

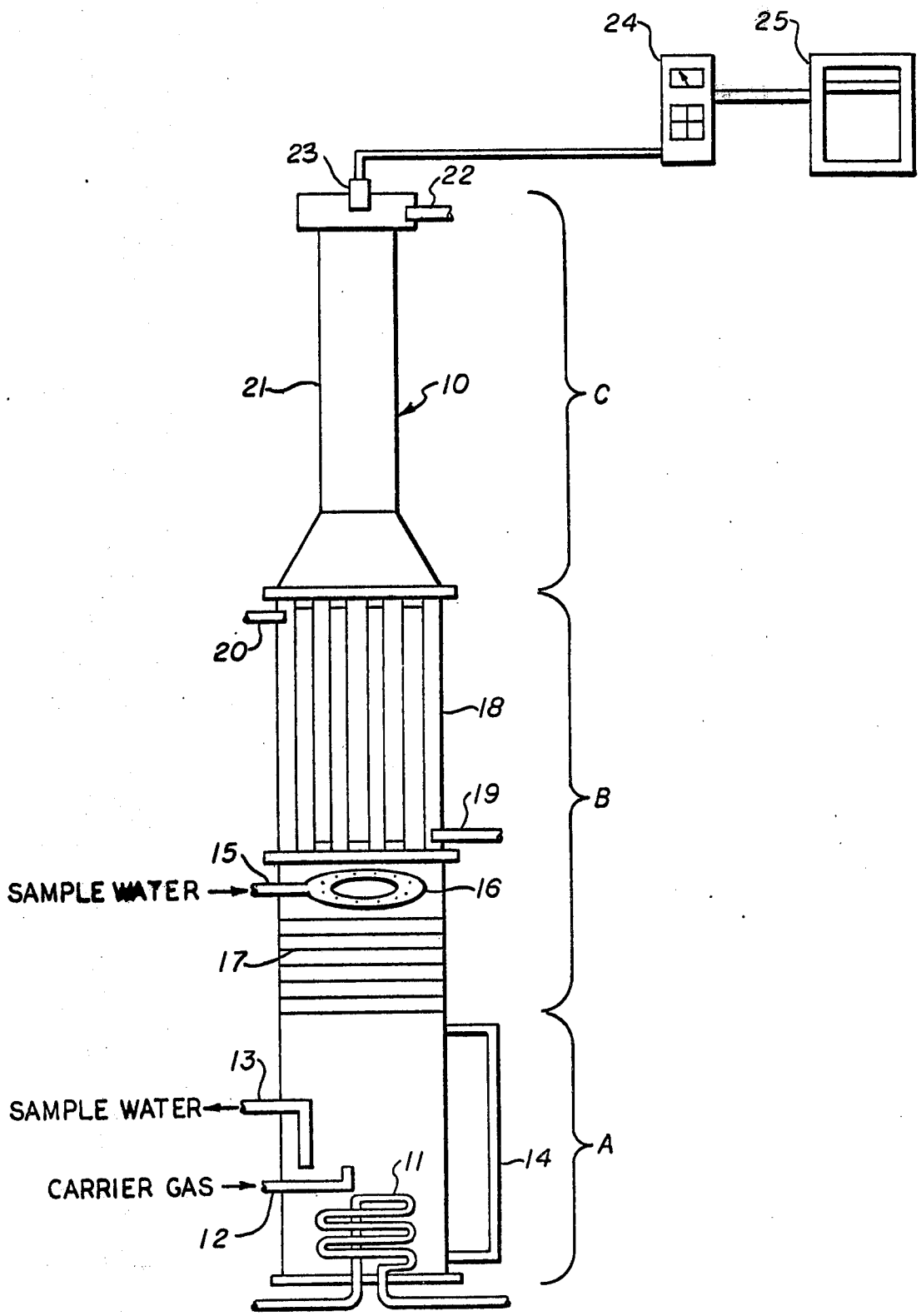

APPARATUS AND METHOD FOR THE DISCOVERY OF VOLATILE ORGANIC COMPOUNDS IN WATER

BACKGROUND OF THE INVENTION

The present invention relates to an apparatus for detecting small amounts of organic compounds in water. More particularly, the invention relates to an apparatus for detection of hydrocarbons which may contaminate process water such as that used for heat exchange cooling of reactors, condensation units and the like.

Enormous volumes of water are employed in various petro-chemical and hydrocarbon manufacturing and refining processes. Normally one stream of water will serve several functions in order to conserve water and energy. For example, a stream of process water from a surface or ground source may first be employed to indirectly cool and condense a hydrocarbon product stream by passing the water and hydrocarbon product stream through indirect heat exchange. The heated water is frequently used as a feed for the production of steam to drive compressors, electric turbines and the like, condensed and recycled. Some cooling is carried out in open cooling towers, where water towers are open to the atmosphere. Some of the water may vaporize to the atmosphere while other portions are recovered for further use.

The problem arises when, through some malfunction or equipment leakage, the water becomes contaminated with organic materials, frequently hydrocarbons. Since ultimately, the water may be returned to the environment, even small quantities of organic material are not desirable. Furthermore, the presence of organic materials in the water indicates a leak or other malfunction, which if not found and corrected, could become a major break down of the equipment.

It is an advantage of the present invention that a continuous method of monitoring a water stream for organic contaminates is provided. It is a particular feature of the present invention that it combines well known and simple components into a simple reliable apparatus. These and other advantages and features will become apparent from the following description.

SUMMARY OF THE INVENTION

Briefly stated, the present invention is an apparatus for discovering trace amounts of volatile organic compounds in water comprising a column having a lower zone containing a heating means, a sample water outlet means and a carrier gas inlet means located therein, an intermediate zone containing a condenser and sample water inlet means located therein, said sample water inlet means being positioned below said condenser and an upper zone having a gas detection means connected thereto.

The lower zone may have the carrier gas inlet means located at the bottom or at some other point provided that the location of the carrier gas inlet is below the sample water outlet, thereby allowing the carrier gas to pass through a portion of the sample water contained therein. The passage of the carrier gas through the water aids in stripping out volatile organic compounds. The carrier gas may be air, when the detection means operates by burning of the volatile organic compounds or it may be an inert gas if a chromatography column is used in the detection process.

In the intermediate zone, the condenser is operated to condense any water vapor and return it to the lower zone of the column but not any volatilized organic compounds. The sample water inlet means is located below the condenser but above the lower zone. Preferably a sparge or spray means is employed to provide a larger surface of water area for the carrier gas to contact and thereby facilitate removing any volatile organic compounds in the water. The condenser is conveniently water cooled.

There are preferably baffle means located below the water inlet means to provide contact surfaces, which will become heated by the passage of the carrier gas from the heated portion of the column, where some of the lower boiling organic compounds will vaporize.

The volatile organic compounds are those having boiling points below that of water under the conditions of pressure in the column. Generally the column would be operated under substantially atmospheric conditions and the temperature in the lower zone will be below 212° F., i.e., up to 212° F. or more preferably from about 160°–180° F. when the pressure is 760 mm of Hg. Most frequently, the organic compounds are hydrocarbons. The apparatus is quite sensitive and will detect trace amounts of less than 100 ppm of the organic compounds in water.

The method of discovering trace amounts of organic compounds in water is also an aspect of the present invention.

BRIEF DESCRIPTION OF THE DRAWINGS

The drawing is a cross sectional elevation of a one embodiment of the present invention.

DETAILED DESCRIPTION OF THE INVENTION AND A PREFERRED EMBODIMENT

Referring to the drawing, the apparatus 10 is shown as a substantially vertical arrangement of components, comprising three zones. In the lower zone A, a heating means 11 which is a steam line is provided at the bottom of the apparatus. A sample water outlet 13 extends into lower zone and a carrier gas inlet 12 located below the sample water outlet 13. A sight glass 14 for determining the water level in the lower zone, extends over sustantially the entire lower zone A.

Above lower zone A is an intermediate zone B which contains sample water inlet 15 and sparge 16. Below the sparge 16 and above zone A are a series of baffles 17. Situated above sparge 16 is condenser 18, which is conveniently cooled with water by inlet and outlet 19 and 20, respectively.

The upper zone C comprises a gas chamber 21 which has a gas outlet 22 and gas detection means 23.

In this embodiment the gas detection means 23 is connected to an indicator 24 and a recorder 25.

The apparatus can be better understood by following its operation. A water sample for examination is fed via line 15 and through sparge 16 and down through baffles 17. The desired level of sample water is obtained in the lower zone A and maintained by adjusting the flow of water into the apparatus to match the flow out via line 13. The water is maintained at a temperature of from 150° F. up to less than 212° F. under atmospheric conditions of pressure (760 mm of Hg), preferably 160°–180° F. by adjustment of the heating means 11. Under such temperature and pressure conditions coupled with the stripping effect of the carrier gas entering through line 12, large numbers of organic compounds, especially hydrocarbons having three to seven carbon atoms are volatilized and carried upward. The system may be operated at sub or super atmospheric pressures, and the temperature will be adjusted accordingly to correspond to the ranges at 760 mm to be below the boiling point of water.

The upward moving gases tend to contact the baffles and the incoming sample water heating it and stripping out volatile organic compounds.

The incoming carrier gas may be sparged into the water by means similar to that shown for the incoming water sample. The carrier gas is selected to accommodate the detection system. For example, an inert gas such as nitrogen is employed if the detection means employs a gas chromatograph, whereas if a detection device which burns the organic compound is employed, then an oxygen containing gas, such air is employed. Carrier gas rates are generally in the range of 0.1 to 10.0 standard cubic feet per hour.

The carrier gas, stripped volatile organic compounds and some water vapor pass up through the condenser 18, which is operated at temperatures to cause condensation of substantially all of the water vapor while not condensing the volatilized organic compounds. This is most easily determined for each apparatus, particularly in regard to the size of the condenser, the operating temperature of lower zone A of the apparatus and the nature of the organic compounds likely to be present.

The uncondensed gases (carrier and volatile organic compounds) pass into the gas chamber 21 where some will enter or contact the detection device 23. A Bacharach Instrument Co., hydrocarbon gas detector No. 800-080.50 has been used to detect trace amounts of $C_4$ hydrocarbons in sample water streams. This particular detector uses a hot wire which contacts the hydrocarbons and burns them, causing a variation in a current in the wire which is amplified, reported and recorded. The gases, i.e., carrier gas, burned sample gases and unburned sample gases leave the apparatus via line 22.

The invention claimed is:

1. An apparatus for discovering trace amounts of volatile organic compounds in water comprising:
   a column having a lower zone containing a heating means, a sample water outlet means and a carrier gas inlet means located therein,
   an intermediate zone containing a condenser and sample water inlet means located therein, said sample water inlet means being positioned below said condenser and
   an upper zone having a gas detection means connected thereto.

2. The apparatus according to claim 1 wherein said carrier gas inlet means is located below said sample water outlet.

3. The apparatus according to claim 2 wherein said carrier gas inlet means is located at the bottom of said lower zone.

4. The apparatus according to claim 1 wherein said sample water inlet means includes a sparge means.

5. The apparatus according to claim 4 wherein baffle means are located in said intermediate zone below said sample water inlet means.

6. The method of discovering the presence of trace amounts of organic compounds in water comprising
   feeding a sample of liquid water containing trace amounts of organic compounds having boiling points lower than water to an intermediate zone,
   passing said liquid water into a lower zone in counter current flow with a carrier gas from said lower zone, said carrier gas passing through said intermediate zone,
   retaining a portion of said liquid water in said lower zone and passing said carrier gas therethrough prior to said carrier gas contacting said liquid water flowing from said intermediate zone,
   maintaining said retained portion of liquid water in said lower zone at a temperature less than the boiling point of said water,
   condensing water from said counterflowing carrier gas in said intermediate zone above said liquid water feeding,
   passing said counterflowing carrier gas into an upper zone and
   contacting said carrier gas with means for detecting gaseous organic compounds.

7. The method according to claim 6 wherein said organic compounds are $C_3$ to $C_7$ hydrocarbons.

8. The method according to claim 6 wherein said temperature in said liquid water in said lower zone is in the range of 150° to less than 212° F. when the pressure is 760 mm of Hg.

9. The method according to claim 8 wherein said temperature in said liquid water in said lower zone is in the range of 150° to 180° F. when the pressure is 760 mm of Hg.

10. The method according to claim 6 wherein said carrier gas is air.

* * * * *